United States Patent
Gueniche et al.

(10) Patent No.: US 9,782,611 B2
(45) Date of Patent: *Oct. 10, 2017

(54) TREATMENT OF GREASY SKIN WITH A BACTERIAL LYSTATE

(75) Inventors: Audrey Gueniche, Rueil-Malmaison (FR); Isabelle Castiel, Nice (FR); Dominique Bernard, Vanves (FR)

(73) Assignee: L'OREAL, Paris (FR)

(*) Notice: Subject to any disclaimer, the term of this patent is extended or adjusted under 35 U.S.C. 154(b) by 322 days.

This patent is subject to a terminal disclaimer.

(21) Appl. No.: 12/607,170

(22) Filed: Oct. 28, 2009

(65) Prior Publication Data

US 2010/0278793 A1    Nov. 4, 2010

Related U.S. Application Data

(60) Provisional application No. 61/111,432, filed on Nov. 5, 2008.

(30) Foreign Application Priority Data

Oct. 28, 2008 (FR) .................... 08 57336

(51) Int. Cl.
*A61Q 19/00* (2006.01)
*A61K 8/99* (2017.01)
*A61K 35/744* (2015.01)

(52) U.S. Cl.
CPC .............. *A61Q 19/008* (2013.01); *A61K 8/99* (2013.01); *A61K 35/744* (2013.01)

(58) Field of Classification Search
CPC ................ C12R 1/01; C12R 1/07; C12N 1/20
USPC ........ 424/93.4, 78.02; 435/243, 252.1, 252.9
See application file for complete search history.

(56) References Cited

U.S. PATENT DOCUMENTS

| | | |
|---|---|---|
| 4,464,362 A | 8/1984 | Kludas et al. |
| 5,756,088 A | 5/1998 | Matsuura et al. |
| 6,040,347 A * | 3/2000 | Cupferman et al. ........... 514/723 |
| 2003/0049231 A1* | 3/2003 | Baur et al. .................... 424/93.4 |
| 2006/0008453 A1 | 1/2006 | Breton et al. |
| 2006/0171936 A1 | 8/2006 | Gueniche et al. |
| 2008/0206171 A1 | 8/2008 | Gueniche |
| 2009/0068161 A1* | 3/2009 | Gueniche et al. .......... 424/93.42 |
| 2010/0272839 A1 | 10/2010 | Gueniche et al. |
| 2011/0014248 A1* | 1/2011 | Castiel et al. ................ 424/401 |

FOREIGN PATENT DOCUMENTS

| | | |
|---|---|---|
| EP | 0 043 128 | 1/1982 |
| EP | 0 852 949 | 7/1998 |
| EP | 1 110 555 | 6/2001 |
| EP | 1 236 463 A1 | 9/2002 |
| EP | 1 609 463 | 12/2005 |
| EP | 1 642 570 | 4/2006 |
| EP | 2 876 029 | 4/2006 |
| EP | 1 731 137 | 12/2006 |
| FR | 2 912 917 | 8/2008 |
| JP | 57-500830 A | 5/1982 |
| JP | 2002-255777 A | 9/2002 |
| JP | 2003-518070 A | 6/2003 |
| JP | 2006-219414 A | 8/2006 |
| JP | 2008-515792 A | 5/2008 |
| WO | WO 82/00093 A1 | 1/1982 |
| WO | WO 01/45721 A1 | 6/2001 |
| WO | WO 02/28402 | 4/2002 |
| WO | WO 2006/037922 A1 | 4/2006 |

OTHER PUBLICATIONS

U.S. Appl. No. 12/607,142.*
U.S. Appl. No. 12/659,597.*
U.S. Appl. No. 13/056,344.*
U.S. Appl. No. 12/509,756, filed Jul. 27, 2009, Castiel, et al.
U.S. Appl. No. 13/056,344, filed Jan. 28, 2011, Castiel, et al.
Office Action issued Oct. 29, 2013, in Japanese Patent Application No. 2009-246912 with English translation.

* cited by examiner

*Primary Examiner* — Ruth Davis
(74) *Attorney, Agent, or Firm* — Oblon, McClelland, Maier & Neustadt, L.L.P.

(57) ABSTRACT

The present invention relates to the cosmetic treatment of greasy skin and/or skin that tends to be greasy with a lysate of at least one microorganism of the genus *Bifidobacterium* species and/or a fraction thereof, as an active.

15 Claims, No Drawings

TREATMENT OF GREASY SKIN WITH A BACTERIAL LYSTATE

CROSS-REFERENCE TO RELATED APPLICATIONS

This application claims priority to U.S. provisional application Ser. No. 61/111,432, filed Nov. 5, 2008; and to French patent application 08 57336, filed Oct. 28, 2008, both incorporated herein by reference.

FIELD OF THE INVENTION

The present invention relates to the area of cosmetic and/or dermatological products, more particularly those intended for the care of greasy skin.

In particular, the present invention aims to propose the use of a novel active for preventing and/or treating disorders associated with greasy skin, notably by an effect of reducing the secretion of sebum.

BACKGROUND OF THE INVENTION

Sebum normally constitutes a hydrating agent of the epidermis.

It is the natural product of the sebaceous gland, which is an appendage of the pilosebaceous unit. It is essentially a more or less complex mixture of lipids. Classically, the sebaceous gland produces squalene, triglycerides, aliphatic waxes, cholesterol waxes, and possibly free cholesterol (Stewart, M. E., Semin Dermatol 11, 100-105(1992)). The action of bacterial lipases converts a variable proportion of the triglycerides formed to free fatty acids.

The sebocyte constitutes the working cell of the sebaceous gland. The production of sebum is associated with a programme of terminal differentiation of this cell. During this differentiation, the metabolic activity of the sebocyte is essentially directed towards the biosynthesis of lipids (lipogenesis) and more precisely towards fatty acid neosynthesis.

Greasy hyperseborrhoeic skin is characterized by excessive secretion and excretion of sebum. Classically, an amount of sebum greater than 200 µg/cm$^2$ measured on the forehead is regarded as characteristic of greasy skin. Such skin is in addition often associated with deficiency of desquamation, a glistening complexion, a thick skin texture, manifestations that are regarded as skin imperfections or aesthetic disorders.

Apart from its aspect of unsightliness, it is an area where complications may develop. It affects the zones where there is a high density of sebaceous glands and results principally from androgenic overstimulation of sebaceous production by these specific glands. Thus, hyperseborrhoea may also participate in the appearance of the lesions of acne vulgaris.

Acne vulgaris is a multifactorial disease that affects the areas of the skin with a high density of sebaceous glands (face, scapular region, arms and intertriginous regions). It is one of the commonest dermatoses.

In its mildest form, this dermatosis affects almost every human being. It is commonest at puberty, but it can be manifested for the first time starting from age 7 to 9 years and up to ages greater than 40 years. Moreover, it affects both men and women.

Among its commonest forms, we may mention acne simplex (acne vulgaris), generally called common acne, acne papulosa and/or nodular acne, acne conglobata and "exogenous" acne, appearing as a reaction to external inflammatory factors.

More precisely, acne is a disease of the follicle of the sebaceous gland. The following five pathogenic factors play a determining role in the constitution of acne:
- genetic predisposition,
- overproduction of sebum (seborrhoea),
- androgenic,
- disorders of follicular keratinization (comedogenesis), and
- bacterial colonization and inflammatory factors.

In fact, in the deepest parts of the infundibular portion of the hair follicle, we find there is formation of an above-normal quantity of keratinocytes. These cells differentiate into horn cells which progressively obstruct the lumen of the follicular canal. The physiological process of continuous desquamation from the acro-infundibulum to the surface is disturbed by the increased adherence of the horn cells produced. There is formation of a hyperkeratosic plug, constituting the comedo, the initial lesion of acne. Finally the three predominant local bacteria, *Staphylococcus epidermidis*, *Malassezia furfur* and *Propionibacterium acnes* find an ideal nutrient medium in the sebaceous follicle. The change in the environment and improvement of the conditions for growth of the microflora lead to an increase in pro-inflammatory products such as lipases, proteases, and interleukins. It is assumed that the lipases produced cause dissociation of the triglycerides to free fatty acids which, acting as irritants to the follicular epithelium, subsequently stimulate hyperproliferation. Promoting intensification of the inflammatory process, the granulocytes are attracted and migrate into the lumen of the follicle, where they finally contribute to the enzymatic disruption of the follicle wall.

The clinical manifestations of so-called retention that occur can be of the open or closed comedo type (microcyst, microcomedo, whitehead). The inflammatory lesions resulting from retention lesions can be papules, pustules, with indurated nodules, abscesses, fistulae, cicatricial states.

Thus, subjects with acne or who are susceptible to acne most often have greasy skin, skin that tends towards greasiness, or mixed. Their skin is most often glistening with numerous imperfections including those of the face (microcyst, microcomedo, whitehead, papules, pustules, with indurated nodules, abscesses, fistulae, and cicatricial states). The imperfections can also include skin that is sallow, with a muddy complexion, with dyschromia, redness, and rough skin with plaques of dry skin. There is cutaneous hyperkeratosis, on the face the pores are dilated, and the skin is often rough with a thick stratum corneum showing areas of dry skin in patches (epidermal atrophy and mild desquamation).

Accordingly, hyperseborrhoea is clearly a biological phenomenon that appears to require effective control to prevent the manifestation of associated skin disorders.

To combat hyperseborrhoea, various compounds have already been proposed which, by topical application on the skin, are able to reduce lipogenesis in the sebocytes and hence limit the production of sebum.

Unfortunately the treatments currently available are not completely satisfactory, notably with regard to side effects with which they are frequently associated such as irritation with certain topical products such as the retinoids and benzoylperoxides, or even gastrointestinal side effects (oral antibiotic therapy). Moreover, resistance of *P. acnes* to certain local antibacterial therapies is often observed.

SUMMARY OF THE INVENTION

Therefore there is still a need for new actives capable of exerting a beneficial cosmetic or therapeutic action on greasy skin or skin that tends to be greasy.

The greasy skins considered in the instant invention may be acned (or acneic) greasy skins or non-acned (or non-acneic) greasy skins.

Also, a greasy skin considered in the instant invention may be a greasy skin associated or not associated with an infected skin.

There is also still a need for actives that make it possible to reestablish the ecoflora of greasy skin.

There is also a need for effective new compositions for preventing and/or treating greasy skin or skin that tends to be greasy and which are pleasant and comfortable in use, thus promoting compliance with the treatment.

There is also a need for novel actives that are able to prevent and/or treat the disorders of greasy skin, notably such as seborrhoeic dermatitides and in particular acne.

The present invention has the aim of satisfying these needs.

Thus, according to a first object, the invention relates to the cosmetic use of an effective amount of a lysate of at least one microorganism of the genus *Bifidobacterium* species and/or a fraction thereof, as an active, for treating and/or preventing greasy skin or skin that tends to be greasy and the associated disorders.

More particularly, the invention relates to a cosmetic method for treating and/or preventing greasy skin or skin that tends to be greasy and the associated skin disorders, comprising at least one stage of administering to an individual in need thereof, as an active, an effective amount of a lysate of at least one microorganism of the genus *Bifidobacterium* species and/or a fraction thereof.

According to a preferred embodiment, the invention relates to the use of a lysate of at least one microorganism of the genus *Bifidobacterium longum*.

According to another embodiment, the invention relates to the acned or non-acned greasy skins, and preferably to non-acned greasy skins.

According to another embodiment, the invention relates to the acned or non-acned, uninfected, greasy skins, and preferably to non-acned, uninfected, greasy skins.

In particular, such skins are characterized by imperfections which may result in skin that is sallow or with a muddy complexion, and possibly displaying dyschromia, redness, and a rough aspect, or plaques of dry skin.

DETAILED DESCRIPTION OF THE INVENTION

The inventors in fact found that said lysate proves effective for the prevention and/or treatment of the disorders associated with greasy skin and/or skin with a tendency to be greasy.

In the sense of the present invention, "skin" means the skin of the face or of the body.

Within the meaning of the invention, "non-acned" or "non-acneic" greasy skin means skins are intended to mean a skin displaying an excessive secretion and excretion of sebum, for example due to an hormonal imbalance or an endocrine disorder, or to environmental factors, such as hot and humid environments, or to the take of tobacco, the stress, the pollution or to the hard water, and being devoid of any signs of acne as defined hereafter.

"Effective amount" means, in the sense of the present invention, a sufficient amount to obtain the expected effect.

In the sense of the present invention, the term "prevent" means the fact of reducing the risk of manifestation of the disorder in question.

As far as the inventors are aware, this efficacy of a lysate of microorganisms of the genus *Bifidobacterium* species has never been described.

Admittedly the application of a lysate of microorganism such as the lysate Repair Complex CLR is known from EP 0 043 128, but only for the purposes of repairing the DNA of the skin cells.

However, the following documents propose the application of microorganisms, essentially for purposes of treatment of dry and/or sensitive skin and associated disorders but with a different form of lysate.

Thus, document WO 02/28402 describes how probiotic microorganisms can have a beneficial effect in controlling reactions of skin hypersensitivity such as the inflammatory and allergic reactions that result from an immunological process. A study concerning the effect of probiotics on infantile immune mechanisms, for example atopic dermatitis, is also reported in "Probiotics in the management of atopic eczema, Clinical and Experimental Allergy 2000", Volume 30, pages 1604-1610. U.S. Pat. No. 5,756,088 describes a diet, notably comprising a polyunsaturated fatty acid and/or biotin, and a *Bifidobacterium*, that has prophylactic and therapeutic effects on animal dermatoses. Documents EP 1 609 463, EP 1 642 570, EP 1 731 137 and FR 2 876 029 describe compositions combining one or more probiotic microorganism(s) with an inorganic cation for the treatment of sensitive skin. As for document PCT/FR2006/050768, it proposes a combination of a probiotic microorganism with a polyunsaturated fatty acid and/or ester of polyunsaturated fatty acid for the treatment of sensitive skin associated with dry skin.

Accordingly, none of these documents describes the application of a microorganism of the genus *Bifidobacterium* species, and even less a lysate according to the invention, as active that can be used for the treatment and/or prevention of greasy skin and/or skin with a tendency to be greasy and associated skin disorders.

The invention also relates to the cosmetic use, preferably by the topical route, of an effective amount of a lysate of at least one microorganism of the genus *Bifidobacterium* species and/or a fraction thereof, as an active for preventing and/or treating the seborrhoeic dermatoses associated with greasy skin or skin that tends to be greasy.

Notably the dermatosis may be acne.

According to another embodiment, the invention relates to the prevention and/or treatment of seborrhoeic dermatoses associated with non-acned greasy skin or non-acned skin that tends to be greasy.

The present invention also relates to the cosmetic use of the aforementioned lysate as an active for preventing and/or treating the lesions and/or imperfections of greasy skin or skin that tends to be greasy and in particular the lesions due to retention of the open or closed comedo type (microcyst, microcomedo, whiteheads) and/or the imperfections such as sallow, glistening skin or muddy complexion, dyschromia, redness, rough skin, possibly with plaques of dry skin.

According to a particular embodiment, the invention relates to the use of the aforementioned lysate for the preparation of a composition, notably dermatological, for preventing and/or treating greasy skin or skin that tends to be greasy and the associated disorders, for example dermatoses, notably of the seborrhoeic type, and in particular acne.

It relates in particular to the use of said lysate for the preparation of a composition, notably dermatological, intended for the treatment or prevention of acne, and in particular of acne vulgaris, acne papulosa and/or nodular acne, acne conglobata and exogenous acne.

Such dermatoses may be benign, caused by excessive proliferation of a fungus and/or yeast and notably yeast of the genus *Malassezia*.

According to another embodiment, the invention relates to the use of the aforementioned lysate for the preparation of a composition, in particular a dermatological composition, for preventing and/or treating non-acned greasy skin or non-acned skin that tends to be greasy and the associated disorders, for example dermatoses, notably of the seborrhoeic type, different from the acne.

Now, as follows from the data presented in the examples, the inventors have notably characterized the capacity of certain of these microorganisms for stimulating the synthesis of a surprising number of proteins that are able to promote and reinforce the antimicrobial defences of the epidermis.

In particular, the inventors showed that a lysate of *Bifidobacterium longum* was able to stimulate the expression of various proteins of the antimicrobial defences of the epidermis such as Ribonuclease 7 (Uniref accession No. Q9H1E1), dermcidin (P81605), prolactin-inducible protein (P12273), proteins S100 A8 and A9 (P05109 and P06702), and the protein histone (Q5R2W0), which can reinforce the defences of the epidermis against excessive colonization by pathogenic microorganisms.

Now, this stimulation of the aforementioned proteins has the advantage of effectively countering colonization of the epidermis by the microorganisms *Malassezia furfur* and *Propionibacterium acnes* responsible for the skin disorders associated with greasy skin and/or skin with a tendency to be greasy. This decrease obtained by means of the lysate according to the invention therefore helps to reestablish a balanced ecoflora with consequent reduction of inflammatory states of the skin and control of seborrhoea. In consequence, imperfections are reduced, the complexion becomes clearer and more uniform, without areas of dyschromia or dryness.

A treatment according to the invention can be even more effective against acne and imperfections of the facial skin if the lysate combines, with its properties of stimulation of the elements of epidermal defence, properties of stimulation of the synthesis of proteases involved in the phenomenon of desquamation (KLK7 (P49862), KLK5 (Q9Y337), Cathepsin L2 (O60911)) as demonstrated by the increase in fragments of proteins of the corneodesmosomes (DSG1 (Q02413), DSC1a (Q9HB01), Cdsn (Q15517) induced by the lysate. The keratinous plug of the comedo can, it seems, then be removed quickly by the action of these proteolytic enzymes, avoiding the creation of a closed medium favourable to bacterial development and then inflammation.

The present invention also relates to the use of a lysate according to the invention for the preparation of a composition, notably dermatological, intended to control seborrhoea.

It further relates to the cosmetic use of an effective amount of a lysate of at least one microorganism of the genus *Bifidobacterium* species and/or a fraction thereof, as active, intended to maintain and/or restore the homeostasis of the skin.

A use according to the invention can, moreover, comprise the application of a lysate of at least one microorganism of the genus *Bifidobacterium* species, in combination with an effective amount of at least one additional, notably probiotic microorganism, different from said lysate.

In the sense of the invention, the expression "different from said lysate" signifies that it is possible to distinguish, within the composition, either two different microorganisms or two different forms of one and the same microorganism.

Thus, when the additional microorganism is of the genus *Bifidobacterium* species and corresponds to the same species as that present in the lysate required according to the invention, said additional microorganism is then present in a form other than a lysate, for example in a live form.

A use according to the present invention can, moreover, comprise the application of a lysate of at least one microorganism of the genus *Bifidobacterium* species, in combination with an effective amount of at least one active intended for reducing and/or correcting the excessive secretion of sebum, for example an antiseborrhoeic active, notably as described below.

According to another of its aspects, the present invention relates to a cosmetic and/or dermatological composition that can be used for preventing and/or treating greasy skin or skin that tends to be greasy and the associated aesthetic disorders, comprising in a physiologically acceptable medium, at least an effective amount of a lysate of at least one microorganism of the genus *Bifidobacterium* species, in combination with at least one antiseborrhoeic active, notably as described below.

According to another of its aspects, the invention relates to a method, notably cosmetic, for preventing and/or treating greasy skin or skin that tends to be greasy and the associated, notably aesthetic, skin disorders in a subject, comprising at least one stage of administration of an effective amount of a lysate of at least one microorganism of the genus *Bifidobacterium* species or fractions thereof to said subject.

According to a variant embodiment of the invention, a lysate according to the invention can be applied by the oral route.

According to another variant embodiment of the invention, the lysate according to the invention can be applied by the topical route.

As described below, the compositions containing it are formulated so as to be compatible with the method of administration adopted.

Lysate of Microorganism(s)

As stated previously, the microorganisms of the genus *Bifidobacterium* species used as active according to the invention are employed in the form of a lysate.

A lysate commonly denotes a material obtained after the destruction or dissolution of biological cells by a phenomenon called cell lysis, thus causing the release of the intracellular biological constituents naturally contained in the cells of the microorganism in question.

In the sense of the present invention, the term lysate is used without distinction to denote all of the lysate obtained by lysis of the microorganism in question or only a fraction thereof.

Thus, the invention relates to the application of a lysate of *Bifidobacterium* species and/or a fraction thereof.

The lysate used is therefore formed wholly or partly from the intracellular biological constituents and the constituents of the cell walls and membranes.

More precisely, it contains the cellular cytoplasmic fraction containing the enzymes such as lactic acid dehydrogenase, the phosphatases, the phosphoketolases, transaldolases and the metabolites. For purposes of illustration, the constituents of the cell walls are notably peptidoglycan, murein or mucopeptide and teichoic acid and the constituents of the cell membranes are composed of glycerophospholipids.

This cell lysis can be performed by various technologies, for example osmotic shock, thermal shock, with ultrasound, or under mechanical stress such as centrifugation.

According to a preferred embodiment, the lysate is obtained by lyse with ultrasound.

More particularly, said lysate can be obtained according to the technology described in U.S. Pat. No. 4,464,362, and notably according to the following protocol.

The microorganism of the *Bifidobacterium* species type considered is cultivated anaerobically in a suitable culture medium, for example according to the conditions described in documents U.S. Pat. No. 4,464,362 and EP 0 043 128. When the stationary phase of development is reached, the culture medium can be inactivated by pasteurization, for example at a temperature of 60 to 65° C. for 30 min. The microorganisms are then collected by a conventional separation technique, for example membrane filtration, centrifugation and resuspension in a sterile physiological NaCl solution. The lysate can be obtained by ultrasonic disintegration of said medium in order to release its cytoplasmic fractions, the fragments of cell wall and the products resulting from metabolism. Then all the components in their natural distribution are stabilized in a weakly acid aqueous solution.

In this way a lysate is generally obtained that has a concentration of the order of 0.1 to 50%, in particular from 1 to 20%, and notably about 5% by weight of active substance(s) relative to its total weight.

The lysate can be used in various forms, in the form of a solution or in a pulverulent form.

A microorganism belonging to the genus *Bifidobacterium* species is more particularly selected from the species: *Bifidobacterium longum*, *Bifidobacterium bifidum*, *Bifidobacterium breve*, *Bifidobacterium animalis*, *Bifidobacterium lactis*, *Bifidobacterium infantis*, *Bifidobacterium adolescentis*, *Bifidobacterium pseudocatenulatum*, and mixtures thereof.

The species *Bifidobacterium longum* is quite particularly suitable for the invention.

It can advantageously be the lysate registered under the INCI name: Bifidat ferment Lysate, under the EINECS name: *Bifidobacterium longum*, under the EINECS No.: No. 306-168-4 and under the CAS No.: No. 96507-89-0.

The product marketed under the designation Repair Complex CLR® by the company K. RICHTER GmbH and that is formed of an inactivated lysate of the species *Bifidobacterium longum* falls within the scope of the invention.

The active forming the lysate and belonging to the genus *Bifidobacterium* species can be formulated in a composition at a rate of at least 0.0001% (expressed in dry weight), in particular at a rate from 0.001 to 20% and more particularly at a rate from 0.01 to 2% of dry weight of active substance relative to the total weight of the carrier or of the composition containing it.

The lysate content for the topical route according to the invention can vary from 0.0001 to 30% by weight, notably from 0.01 to 15% by weight, and in particular from 0.1 to 10% by weight relative to the total weight of the composition containing it.

In the particular case when the lysate is intended for oral administration, the concentration of lysate can be adjusted so as to correspond to doses (expressed in equivalent of microorganism) ranging from $5.10^2$ to $10^{13}$ CFU/d and in particular from $10^5$ to $10^{11}$ CFU/d.

According to a variant of the invention, a lysate suitable for the invention is used in combination with at least one other microorganism.

Thus, the invention relates to the use, in addition to a microorganism of the genus *Bifidobacterium* species, of at least an effective amount of at least one additional microorganism, notably of probiotic type, and/or a fraction thereof, different from said lysate.

In the sense of the present invention, "probiotic microorganism" means a live microorganism which, when it is consumed in an appropriate amount, has a positive effect on the health of its host "Joint FAO/WHO Expert Consultation on Evaluation of Health and Nutritional Properties of Probiotic in Food Including Powder Milk with Live Lactic Acid Bacteria, 6 Oct. 2001", and which can in particular improve the intestinal microbial balance.

These microorganisms suitable for the invention can be selected notably from the ascomycetes such as *Saccharomyces*, *Yarrowia*, *Kluyveromyces*, *Torulaspora*, *Schizosaccharomyces pombe*, *Debaryomyces*, *Candida*, *Pichia*, *Aspergillus* and *Penicillium*, bacteria of the genus *Bacteroides*, *Fusobacterium*, *Melissococcus*, *Propionibacterium*, *Enterococcus*, *Lactococcus*, *Staphylococcus*, *Peptostreptococcus*, *Bacillus*, *Pediococcus*, *Micrococcus*, *Leuconostoc*, *Weissella*, *Aerococcus*, *Oenococcus*, *Lactobacillus*, and mixtures thereof.

As ascomycetes quite particularly suitable for the present invention, we may mention in particular *Yarrowia lipolytica* and *Kluyveromyces lactis*, as well as *Saccharomyces cerevisiae*, *Torulaspora*, *Schizosaccharomyces pombe*, *Candida* and *Pichia*.

Specific examples of additional probiotic microorganisms are *Lactobacillus acidophilus*, *Lactobacillus alimentarius*, *Lactobacillus curvatus*, *Lactobacillus delbrueckii* subsp. *Lactis*, *Lactobacillus gasseri*, *Lactobacillus johnsonii*, *Lactobacillus reuteri*, *Lactobacillus paracasei*, *Lactobacillus rhamnosus* (*Lactobacillus GG*), *Lactobacillus sake*, *Lactococcus lactis*, *Streptococcus thermophilus*, *Staphylococcus carnosus*, and *Staphylococcus xylosus*, and mixtures thereof.

More particularly, they are probiotic microorganisms from the group of the lactic acid bacteria, such as notably *Lactobacillus*.

As an example of these lactic acid bacteria, we may more particularly mention *Lactobacillus johnsonii*, *Lactobacillus paracasei*, *Lactobacillus reuteri*, *Lactobacillus rhamnosus*, and mixtures thereof.

The species that are quite particularly suitable are *Lactobacillus johnsonii*, in particular the strain deposited in accordance with the Budapest treaty with the Institut Pasteur (28 rue du Docteur Roux, F-75024 Paris cedex 15) under the following designation CNCM I-1225.

In general, the compositions for topical application according to the invention generally comprise from 0.0001 to 30%, in particular from 0.001 to 15% and more particularly from 0.1 to 10% of one or more additional, notably probiotic, microorganisms.

This or these microorganism(s) can be included in the compositions according to the invention in a live form, semi-active form or inactivated, dead form.

In the case when the microorganisms are formulated in a composition in live form, the quantity of live microorganisms can vary from $10^3$ to $10^{15}$ CFU/g, in particular from $10^5$ to $10^{15}$ CFU/g and more particularly from $10^7$ to $10^{12}$ CFU/g of microorganisms per gram of composition.

In the particular case when the microorganism(s) is (are) formulated in compositions for administration by the oral route, the concentration of microorganism(s), notably probiotic, can be adjusted so as to correspond to doses (expressed in equivalent of microorganism) ranging from $5.10^5$ to $10^{13}$ CFU/d and in particular from $10^7$ to $10^{11}$ CFU/d.

It (they) can also be included in the form of fractions of cellular components. The microorganism(s), or fraction(s) can also be introduced in the form of a powder, a liquid, a culture supernatant or a fraction thereof, diluted or not, or concentrated or not.

According to one variant, the compositions can also contain a divalent inorganic cation.

Active

Whatever the method of administration considered, the lysate of the invention can advantageously be combined with at least one other active.

Thus, a composition, topical or oral, according to the invention can moreover contain at least one antiseborrhoeic active.

Such a formulation advantageously makes it possible to amplify the beneficial effects of a lysate of the invention.

"Antiseborrhoeic active" means a compound capable of regulating the activity of the sebaceous glands.

An antiseborrhoeic active suitable for the invention can notably be selected from retinoic acid, benzoyl peroxide, sulphur, vitamin B6 (or pyridoxine), selenium chloride, samphire; mixtures of extracts of cinnamon, of tea and of octanoylglycine such as Sepicontrol A5 TEA® from Seppic; the mixture of cinnamon, of sarcosine and of octanoylglycine, marketed notably by the company SEPPIC under the trade name Sepicontrol A5®; zinc salts such as zinc gluconate, zinc pyrrolidone carboxylate (or zinc pidolate), zinc lactate, zinc aspartate, zinc carboxylate, zinc salicylate, zinc cysteate; derivatives of copper and in particular copper pidolate such as Cuivridone® from Solabia; extracts of plants of the species *Arnica montana, Cinchona succirubra, Eugenia caryophyllata, Humulus lupulus, Hypericum perforatum, Mentha piperita, Rosmarinus officinalis, Salvia officinalis* and *Thymus vulgaris*, all marketed for example by the company MARUZEN; extracts of meadowsweet (*Spiraea ulamaria*) such as that sold under the name Sébonormine® by the company Silab; extracts of alga *Laminaria saccharina* such as that sold under the name Phlorogine® by the company Biotechmarine; the mixtures of extracts of burnet roots (*Sanguisorba officinalis/Poterium officinale*), of ginger rhizomes (*Zingiber officinalis*) and of cinnamon bark (*Cinnamomum cassia*) such as that sold under the name Sebustop® by the company Solabia; linseed extracts as sold under the name Linumine® by the company Lucas Meyer; extracts of Phellodendron such as that sold under the name Phellodendron extract BG by the company Maruzen or Oubaku liquid B by the company Ichimaru Pharcos; the mixtures of argan oil, extract of *Serenoa serrulata* (saw palmetto) and sesame seed extract such as that sold under the name Regu SEB® by the company Pentapharm; the mixtures of extracts of epilobe, of *Terminalia chebula*, of nasturtium and of bioavailable zinc (microalgae) such as that sold under the name Seborilys® by the company Green Tech; the extracts of *Pygeum afrianum* such as that sold under the name *Pygeum afrianum* sterolic lipid extract by the company Euromed; the extracts of *Serenoa serrulata* such as those sold under the name Viapure Sabal by the company Actives International, or those sold by the company Euromed; the mixtures of extracts of plantain, of *Berberis aquifolium* and of sodium salicylate such as that sold under the name Seboclear® by the company Rahn; clove extract such as that sold under the name Clove extract Powder by the company Maruzen; argan oil such as that sold under the name Lipofructyl® by Laboratories Sérobiologiques; filtrates of lactic protein such as that sold under the name Normaseb® by the company Sederma; extracts of *alga Laminaria*, such as that sold under the name Laminarghane® by the company Biotechmarine; oligosaccharides of alga *Laminaria digitata* such as that sold under the name Phycosaccharide AC by the company Codif; extracts of cane sugar such as that marketed under the name Policosanol® by the company Sabinsa; sulphonated shale oil, such as that sold under the name Ichtyol Pale® by the company Ichthyol; extracts of meadowsweet (*Spiraea ulmaria*) such as that sold under the name Cytobiol® Ulmaire by the company Libiol; sebacic acid, notably sold in the form of a gel of sodium polyacrylate under the name Sebosoft® by the company Sederma; glucomannans extracted from konjac tuber and modified with alkylsulphonate chains such as that sold under the name Biopol Beta by the company Arch Chemical; extracts of *Sophora angustifolia*, such as those sold under the name *Sophora* powder or *Sophora* extract by the company Bioland; extracts of *Cinchona succirubra* bark such as that sold under the name Red bark HS by the company Alban Muller; extracts of *Quillaja saponaria* such as that sold under the name Panama wood HS by the company Alban Muller; glycine grafted on undecylene chain, such as that sold under the name Lipacide UG OR by the company Seppic; the mixture of oleanolic acid and nordihydroguaiaretic acid, such as that sold in the form of a gel under the name AC.Net by the company Sederma; phthalimidoperoxyhexanoic acid; trialkyl($C_{12}$-$C_{13}$) citrate sold under the name COSMACOL® ECI by the company Sasol; trialkyl($C_{14}$-$C_{15}$) citrate sold under the name COSMACOL® ECL by the company Sasol; 10-hydroxydecanoic acid, and notably mixtures of 10-hydroxydecanoic acid, of sebacic acid and of 1,10-decanediol such as that sold under the name Acnacidol® BG by the company Vincience; and mixtures thereof.

The antiseborrhoeic active is for example present in a content ranging from 0.1 to 10% by weight, preferably from 0.1 to 5% by weight, and more preferably from 0.5 to 3% by weight, relative to the total weight of the composition.

In addition to this seborrhoeic active, the compositions according to the invention can also contain several other actives commonly used and/or permitted.

As actives that are used conventionally, we may mention vitamins B3, B5, B6, B8, C, D, E, or PP, niacin, carotenoids, polyphenols, minerals and trace elements, phytooestrogens, proteins and amino acids, mono- and polysaccharides, amino-sugars, phytosterols and triterpene alcohols of vegetable origin.

The minerals and trace elements particularly employed are zinc, calcium, magnesium, copper, iron, iodine, manganese, selenium, chromium(III).

Among the polyphenols, the polyphenols from grape, tea, olive, cocoa, coffee, apple, bilberry, elder, strawberry, cranberry, and onion are also used in particular. Preferably among the phytooestrogens, the isoflavones are used, in free form or glycosylated, such as genistein, daidzein, glycitein or also lignans, in particular those from flax and from schizandra chinensis.

The amino acids or the peptides and proteins containing them, such as taurine, threonine, cysteine, tryptophan, methionine. The lipids preferably belong to the group of oils containing mono- and polyunsaturated fatty acids such as oleic, linoleic, alpha-linolenic, gamma-linolenic, stearidonic acids, long-chain omega-3 fish fatty acids such as EPA and DHA, conjugated fatty acids obtained from plants or animals such as CLA (conjugated linoleic acid).

In particular, it is possible to use an antioxidant complex comprising vitamins C and E, and at least one carotenoid, notably a carotenoid selected from β-carotene, lycopene, astaxanthin, zeaxanthin and lutein, flavonoids, such as catechins, hesperidin, proanthocyanidins and anthocyanins, lipoic acid and coenzyme Q10.

The additional active can also be at least one prebiotic or a mixture of prebiotics. More particularly, these prebiotics can be selected from oligosaccharides, produced starting from glucose, galactose, xylose, maltose, sucrose, lactose, starch, xylan, hemicellulose, inulin, gums of the acacia type for example, or a mixture thereof.

More particularly, the oligosaccharide comprises at least one fructo-oligosaccharide. More particularly, said prebiotic can comprise a mixture of fructo-oligosaccharide and inulin.

In the topical galenical forms, it is possible to use, more particularly, as hydrophilic actives, proteins or protein hydrolysates, amino acids, polyols notably from $C_2$ to $C_{10}$ such as glycerol, sorbitol, butylene glycol and polyethylene glycol, urea, allantoin, sugars and sugar derivatives, water-soluble vitamins, starch, bacterial or plant extracts such as those from Aloe vera.

As for the lipophilic actives, it is possible to use retinol (vitamin A) and its derivatives, tocopherol (vitamin E) and its derivatives, ceramides, essential and non-saponifiable oils (tocotrienol, sesamin, gamma oryzanol, phytosterols, squalenes, waxes, terpenes).

The product can also be combined advantageously with actives capable of acting:

either directly on desquamation, promoting exfoliation, such as the β-hydroxyacids, in particular salicylic acid and its derivatives (including n-octanoyl-5-salicylic acid); the α-hydroxyacids, such as glycolic, citric, lactic, tartaric, malic or mandelic acids; urea and certain of its derivatives; gentisic acid; the oligofucoses; cinnamic acid; dioic acid; extract of *Saphora japonica*; resveratrol; detergents and certain derivatives of jasmonic acid;

and/or on the activities of the enzymes involved in the degradation of the corneodesmosomes, such as the stratum corneum chymotryptic enzyme (SCCE) or even other proteases (trypsin-like, chymotrypsin-like, cathepsin D) as well as other categories of hydrolases (e.g. glycosidases, ceramidases). We may mention the chelating agents of the mineral salts: EDTA; N-acyl-N,N',N'-ethylenediaminetriacetic acid; aminosulphonic compounds and in particular (N-2-hydroxyethylpiperazine-N-2-ethane) sulphonic acid (HEPES); derivatives of 2-oxothiazolidine-4-carboxylic acid (procysteine); derivatives of alpha amino acids of the glycine type (such as described in EP-0 852 949, as well as sodium methyl glycine diacetate marketed by BASF under the trade name TRILON M); honey; sugar derivatives such as O-octanoyl-6-D-maltose and N-acetyl glucosamine; urea or some of its derivatives, for example Hydrovance; derivatives of C-Glycosides.

Galenical Forms

The compositions according to the invention can be in all the galenical forms normally available for the method of administration adopted.

The carrier can be of varying nature depending on the type of composition considered. The compositions intended for topical administration can be aqueous, aqueous-alcoholic or oily solutions, dispersions of the solution type or dispersions of the lotion or serum type, emulsions of liquid or semi-liquid consistency of the milk type, obtained by dispersion of an oil phase in an aqueous phase (O/W) or vice versa (W/O), or a suspension or emulsion of soft, semi-solid or solid consistency, of the cream type, aqueous or anhydrous gel, or microemulsions, microcapsules, microparticles, or vesicular dispersions of the ionic and/or non-ionic type.

These compositions are prepared according to the usual methods.

These compositions can notably constitute creams for cleaning, peeling, treatment or care for the face, for the hands, for the feet, for the large anatomical folds or for the body (for example day creams, night creams, make-up removal creams, foundation creams, sun creams), make-up products such as liquid foundations, make-up removal milks, body milks for protection or care, after-sun milks; lotions, gels or mousses for care of the skin, such as lotions for cleaning or for disinfection, sun lotions, artificial tanning lotions, compositions for the bath, deodorant compositions containing a bactericide, after-shave gels or lotions, epilatory creams, or compositions against insect bites.

The compositions according to the invention can also consist of solid preparations as constituents of soaps or cleaning bars.

When the composition of the invention is an emulsion, the proportion of the fat phase can be from 5 to 80% by weight, and preferably from 5 to 50% by weight relative to the total weight of the composition. The oils, the emulsifiers and the co-emulsifiers used in the composition in the form of emulsion are selected from those classically used in the area of cosmetics and/or dermatology. The emulsifier and the co-emulsifier can be contained in the composition in a proportion ranging from 0.3 to 30% by weight, and preferably from 0.5 to 20% by weight relative to the total weight of the composition.

When the composition of the invention is a solution or an oily gel, the oil phase can represent more than 90% of the total weight of the composition.

As is known, the galenical forms intended for topical administration can also contain additives that are usual in the cosmetic, pharmaceutical and/or dermatological field, such as hydrophilic or lipophilic gelling agents, hydrophilic or lipophilic actives, preservatives, antioxidants, solvents, perfumes, fillers, filters, bactericides, odour absorbers and colorants. The amounts of these various additives are those classically used in the field in question, for example from 0.01 to 20% of the total weight of the composition. Depending on their nature, these additives can be introduced in the fat phase and/or in the aqueous phase.

As fats for use in the invention, we may mention mineral oils, for example hydrogenated polyisobutene and vaseline oil, vegetable oils, for example a liquid fraction of shea butter, sunflower oil and apricot almond oil, animal oils, for example perhydrosqualene, synthetic oils notably purcelline oil, isopropyl myristate and ethyl hexyl palmitate, unsaturated fatty acids and fluorinated oils, for example perfluoropolyethers. It is also possible to use fatty alcohols, fatty acids for example stearic acid and for example waxes, notably paraffin wax, carnauba wax and beeswax. It is also possible to use silicone compounds such as silicone oils and for example cyclomethicone and dimethicone, waxes, resins and silicone rubbers.

As emulsifiers that can be used in the invention, we may mention for example glycerol stearate, polysorbate 60, the cetylstearyl alcohol/ethoxylated cetylstearyl alcohol mixture with 33 moles of ethylene oxide sold under the designation Sinnowax AO® by the company HENKEL, the mixture of PEG-6/PEG-32/Glycol Stearate sold under the designation Tefose® 63 by the company GATTEFOSSE, PPG-3 myristyl ether, silicone emulsifiers such as cetyldimethicone copolyol and sorbitan mono- or tristearate, the stearate of PEG-40, ethoxylated sorbitan monostearate (20 OE).

As solvents for use in the invention, we may mention the lower alcohols, notably ethanol and isopropanol, propylene glycol.

A composition according to the invention can also contain, advantageously, a thermal and/or mineral water, notably selected from Vittel water, the waters of the Vichy basin and the water from Roche Posay.

As hydrophilic gelling agents, we may mention the carboxylic polymers such as carbomer, the acrylic copolymers such as the acrylate/alkylacrylate copolymers, the polyacrylamides and notably the mixture of polyacrylamide, C13-14-Isoparaffin and Laureth-7 sold under the name Sepigel 305® by the company SEPPIC, the polysaccharides such as the cellulosic derivatives such as the hydroxyalkylcelluloses and in particular hydroxypropylcellulose and hydroxyethylcellulose, the natural gums such as guar gum, carob gum and xanthan gum and the clays.

As lipophilic gelling agents, we may mention the modified clays such as the bentones, the metal salts of fatty acids such as aluminium stearates and hydrophobic silica, or ethylcellulose and polyethylene.

For use by the oral route, the carrier is ingestible.

The ingestible carrier can be of various kinds depending on the type of composition considered.

Notably the following are suitable as food or pharmaceutical carriers: milk, yoghurt, cheese, fermented milks, milk-based fermented products, ices, products based on fermented cereals, milk-based powders, formulas for children and babies, food products of the confectionery type, chocolate, cereals, feed for animals in particular domestic animals, tablets, capsules or lozenges, oral supplements in dry form and oral supplements in liquid form.

The lysate of microorganism of the invention can moreover be formulated with the usual excipients and components for such oral compositions or food supplements, i.e. notably fat and/or aqueous components, humectants, thickeners, preservatives, texture agents, flavouring agents and/or enrobing agents, antioxidants, preservatives and colorants that are usual in the food products area.

The formulating agents and excipients for oral compositions, and notably for food supplements, are known in this field and will not be described in detail here. For ingestion, numerous embodiments of oral compositions and notably of food supplements are possible. They are formulated by the usual methods to produce coated pills, capsules, gels, controlled-release hydrogels, emulsions, tablets, capsules.

In particular, the lysate of microorganism according to the invention can be incorporated in any other forms of food supplements or of enriched foods, for example food bars, or powders, compacted or not. The powders can be diluted with water, in soda, milk products or soya derivatives, or can be incorporated in food bars.

According to a particular embodiment, the additional microorganisms considered according to the invention can be formulated within compositions in encapsulated form for significantly improving their survival time. In such a case, the presence of a capsule can in particular slow down or prevent the degradation of the microorganism in the gastro-intestinal tract.

The method of cosmetic treatment of the invention can be applied, notably by administering the lysate or the cosmetic and/or dermatological compositions as defined above, according to the usual technique for use of these compositions. As an illustration, it is possible to use applications of creams, gels, serums, lotions, make-up removal milks or after-sun compositions on the skin, which represents topical application.

The cosmetic method according to the invention can thus be employed by topical application, daily for example, of the lysate according to the invention.

The method according to the invention can comprise a single application. According to another embodiment, the application is repeated for example 2 to 3 times daily for one day or more and generally for an extended duration of at least 4, or even 1 to 15 weeks.

In the description and in the examples given below, unless stated otherwise, the percentages are percentages by weight and the ranges of values stated in the form "between . . . and . . . " include the lower and upper limits stated. The ingredients are mixed, before being formed, in the order and in conditions that are easily determined by a person skilled in the art.

Moreover, combination treatments optionally with oral or topical forms in order to supplement or reinforce the activity of the lysate as defined by the invention can be envisaged.

Thus, we might envisage a treatment by the topical route with a composition containing the lysate of *Bifidobacterium* combined with a composition for oral or topical application optionally containing another probiotic microorganism or other probiotics in dead, live or semi-active form.

The examples given below are for purposes of illustration and do not limit the scope of the invention.

EXAMPLES

Example 1: Lotion for the Face

| Ingredients | Quantity (%) |
| --- | --- |
| Lysate of *Bifidobacterium longum*\* | 5.00\*\* |
| Anti-inflammatory | 0.05 |
| Antioxidant | 0.05 |
| Isopropanol | 40.00 |
| Preservative | 0.30 |
| Water | Q.s. 100 |

\*It is the lysate registered under the INCI name Bifidat ferment Lysate, used as a formulation with 5% by weight of active.
\*\*amount based on total product Example 2: Gel for Care of the Face

| Ingredients | Quantity (%) |
| --- | --- |
| Lysate of *Bifidobacterium longum*\* | 5.00\*\* |
| Hydroxypropylcellulose (Klucel H ® sold by the company HERCULES) | 1.00 |
| Vitamin E | 2.50 |
| Antioxidant | 0.05 |
| Isopropanol | 40.00 |
| Preservative | 0.30 |
| Water | Q.s. 100 |

\*It is the lysate registered under the INCI name Bifidat ferment Lysate, used as a formulation with 5% by weight of active.
\*\*amount based on total product Example 3: Milk for Care of the Face

| Ingredients | Quantity (%) |
| --- | --- |
| Lysate of *Bifidobacterium longum*\* | 10.00\*\* |
| Glycerol stearate | 1.00 |
| Cetylstearyl alcohol/ethoxylated cetylstearyl alcohol with 3 moles OE (Sinnovax AO ® sold by the company HENKEL) | 3.00 |
| Cetyl alcohol | 1.00 |
| Dimethicone (DC 200 Fluid ® sold by the company Dow Corning) | 1.00 |
| Vaseline oil | 6.00 |
| Isopropyl myristate (Estol IPM 1514 ® sold by the company Unichema) | 3.00 |

-continued

| Ingredients | Quantity (%) |
| --- | --- |
| Glycerol | 20.00 |
| Preservative | 0.30 |
| Water | Q.s. 100 |

*It is the lysate registered under the INCI name Bifidat ferment Lysate, used as a formulation with 5% by weight of active.
**amount based on total product Example 4: Cream for Care of the Face

| Ingredients | Quantity (%) |
| --- | --- |
| Arachidyl behenyl alcohol/arachidylglusoside | 3.00 |
| Isohexadecane | 7.00 |
| Lysate of Bifidobacterium longum* | 10.00** |
| Glycerol | 2.00 |
| Extract of Vitreoscilla filiformis | 3.00 |
| BHT | 0.05 |
| POB methyl | 0.10 |
| POB propyl | 0.50 |
| Water | Q.s. 100 |

*It is the lysate registered under the INCI name Bindat ferment Lysate, used as a formulation with 5% by weight of active.
**amount based on total product Example 5: Gel for Care of the Face

| Ingredients | Quantity (%) |
| --- | --- |
| Extract of Vitreoscilla filiformis | 3.00 |
| Lysate of Bifidobacterium longum* | 10.00** |
| Antioxidant | 0.05 |
| Vitamin C | 2.50 |
| Antioxidant | 0.50 |
| Isopropanol | 40.50 |
| Preservative | 0.30 |
| Water | Q.s. 100 |

*It is the lysate registered under the INCI name Bifidat ferment Lysate, used as a formulation with 5% by weight of active.
**amount based on total product Example 6: Results from Proteomics The product tested is a lysate of Bifidobacterium longum in suspension, disintegrated (by ultrasound) in a weakly acid aqueous medium marketed under the name Repair Complex CLR®.

The active was tested on its own in a randomized, double-blind study.

Sixty-six women with dry skin were divided into two groups, placebo (n=33 group A), Repair Complex CLR® (n=33 group B). The treatments were applied topically for 58 days, the active being formulated at 10% of the test formulation. The carrier formulation is an oil/demineralized water emulsion Arlacel/Myrj® containing 5% Parleam, 15% cyclopentasiloxane, 3% glycerol and 2% vaseline.

In the placebo formulation, the absence of lysate is compensated with water.

The subjects were evaluated on D1, D29, D43, and D57.

The variation of various cutaneous markers was investigated by differential proteomics on samples of isolated stratum corneum.

A sample is taken from the outer surface of the leg at times D1, D29, D43 and D57 by varnish stripping so as to remove only a portion of the stratum corneum, i.e. at most 4 to 5 layers of stratum corneum.

A cloth of nylon filter 41 µm type NY41 Millipore is applied on a previously defined area of the left leg. Then a transparent varnish with the reference 614254/T.D. comprising: nitrocellulose 6.86 g; isopropanol 2.94 g; hypoallergenic alkyl resin 7.35 g; acetyl tributyl citrate 7.7 g; ethyl acetate 75.15 g; is spread by brush (15 mm), and is then left to dry for 15 min. The nylon cloth is then recovered using spring forceps, by smartly pulling away the varnish stripping.

The varnish strippings are stored at −20° C., flat in plastic bags.

These skin samples (varnish stripping of stratum corneum) were then analysed by proteomics using a technique called "isobaric marking", to evaluate the expression of different proteins.

This "isobaric marking" technique or iTRAQ is based on the marking of tryptic peptides with a series of reagents, which are called isobaric as they all have a molecular weight of 145 Da, and form a covalent bond with the primary amines of the amino-terminal end or of the side chain of the lysine residues.

The marked peptides are detected by mass spectrometry with the intrinsic mass of the peptide+145 Da from the reagent. At the stage of fragmentation of the peptide, the contribution of each of the reagents is assessed from the release of ions (fragments) having different specific masses.

Such a method is described in more detail by Zieske (J. Exp. Bot., 2006, 57:1501) or Wiese et al. (Proteomics, 2007, 7:340).

The results of the analysis by proteomics showed that the lysate of Bifidobacterium longum stimulates the expression of some of the antimicrobial defence proteins of the epidermis (RNase 7, Dermcidin, prolactin-inducible protein, fragments of histone, etc.) and certain proteases involved in the phenomenon of desquamation (KLK-7, KLK-5, cathepsin L2, fragments of proteins of the corneodesmosome).

Detection of stimulation of the aforementioned proteins is an indicator of the decrease in colonization by the microorganisms Malassezia furfur and Propionibacterium acnes responsible for skin disorders associated with greasy skin and/or skin with a tendency to be greasy.

Thus, this decrease helps to reestablish a balanced ecoflora, leading to reduction of inflammatory states of the skin and control of seborrhoea. As a consequence, imperfections are reduced, the complexion becomes clearer and more uniform, without areas of dyschromia or dryness.

Moreover, the presence of proteases, characteristic of the phenomenon of desquamation, makes it possible to treat the areas displaying disorders associated with the greasy areas without causing excessive dryness in these areas.

The invention claimed is:

1. A method for treating skin, the method comprising:
   administering to an individual in need thereof, an effective amount of a whole lysate of at least one microorganism of the genus Bifidobacterium selected from the group consisting of Bifidobacterium longum, Bifidobacterium bifidum; Bifidobacterium breve, Bifidobacterium animalis, Bifidobacterium infantis, Bifidobacterium adolescentis, and Bifidobacterium pseudocatenulatum;
   wherein the skin treated is at least one selected from the group consisting of a greasy skin, a skin that tends to be greasy and a skin having a disorder associated with greasy skin or skin that tends to be greasy, and wherein the whole lysate is obtained by ultrasonic disintegration and comprises released cytoplasmic fractions, fragments of cell wall and metabolic products.

2. The method according to claim 1, wherein the treated skin has a skin disorder and the skin disorder is a lesion or imperfection of greasy skin or skin that tends to be greasy, a retention lesion of the open comedo type, or a retention lesion of the closed comedo type.

3. The method according to claim 1, wherein the treated skin has a skin disorder and the skin disorder is at least one skin imperfection selected from the group consisting of sallow, glistening skin, muddy skin, dyschromia, redness, rough skin, and a plaque of dry skin.

4. The method according to claim 1, wherein the treated skin has a skin disorder and the skin disorder is seborrhoeic dermatosis.

5. A method for controlling seborrhea, the method comprising administering to an individual in need thereof a composition comprising, an effective amount of a whole lysate of at least one microorganism of the genus *Bifidobacterium* selected from the group consisting of *Bifidobacterium longum*, *Bifidobacterium bifidum*, *Bifidobacterium breve*, *Bifidobacterium animalis*, *Bifidobacterium infantis*, *Bifidobacterium adolescentis*, *Bifidobacterium pseudocatenulatum*, wherein the seborrhea is of a greasy skin, a skin that tends to be greasy or a skin having a disorder associated with greasy skin or skin that tends to be greasy, and wherein the whole lysate is obtained by ultrasonic disintegration and comprises released cytoplasmic fractions, fragments of cell wall and metabolic products.

6. The method according to claim 1, 4 or 5, wherein the microorganism of the genus *Bifidobacterium* is *Bifidobacterium longum*.

7. The method according to claim 1, 4 or 5, wherein a content of active substance(s) in the whole lysate is from 0.1 to 50% by weight.

8. The method according to claim 1, further comprising: administering with the whole lysate another microorganism, probiotic or a fraction thereof, different from the whole lysate.

9. The method according to claim 4, further comprising: administering with the whole lysate, another microorganism, probiotic or a fraction thereof, different from the whole lysate.

10. The method according to claim 5, further comprising: administering with the whole lysate, another microorganism, probiotic or a fraction thereof, different from the whole lysate.

11. The method according to claim 8, wherein a probiotic microorganism different from the whole lysate is administered and the probiotic microorganism is at least one ascomycete microorganism selected from the group consisting of *Saccharomyces*, *Yarrowia*, *Kluyveromyces*, *Torulaspora*, *Schizosaccharomyces pombe*, *Debaryomyces*, *Candida*, *Pichia*, *Aspergillus* and *Penicillium*, bacteria of the genus *Bacteroides*, *Fusobacterium*, *Melissococcus*, *Propionibacterium*, *Enterococcus*, *Lactococcus*, *Staphylococcus*, *Peptostreptococcus*, *Bacillus*, *Pediococcus*, *Leuconostoc*, *Weissella*, *Aerococcus*, and *Oenococcus*.

12. The method according to claim 9, wherein a probiotic microorganism different from the whole lysate is administered and the probiotic microorganism is at least one ascomycete microorganism selected from the group consisting of *Saccharomyces*, *Yarrowia*, *Kluyveromyces*, *Torulaspora*, *Schizosaccharomyces pombe*, *Debaryomyces*, *Candida*, *Pichia*, *Aspergillus* and *Penicillium*, bacteria of the genus *Bacteroides*, *Fusobacterium*, *Melissococcus*, *Propionibacterium*, *Enterococcus*, *Lactococcus*, *Staphylococcus*, *Peptostreptococcus*, *Bacillus*, *Pediococcus*, *Leuconostoc*, *Weissella*, *Aerococcus*, and *Oenococcus*.

13. The method according to claim 10, wherein a probiotic microorganism different from the whole lysate is administered and the probiotic microorganism is at least one ascomycete microorganism selected from the group consisting of *Saccharomyces*, *Yarrowia*, *Kluyveromyces*, *Torulaspora*, *Schizosaccharomyces pombe*, *Debaryomyces*, *Candida*, *Pichia*, *Aspergillus* and *Penicillium*, bacteria of the genus *Bacteroides*, *Fusobacterium*, *Melissococcus*, *Propionibacterium*, *Enterococcus*, *Lactococcus*, *Staphylococcus*, *Peptostreptococcus*, *Bacillus*, *Pediococcus*, *Leuconostoc*, *Weissella*, *Aerococcus*, and *Oenococcus*.

14. The method according to claim 1, 4 or 5, wherein the whole lysate is administered topically.

15. The method according to claim 1, 4 or 5, wherein the whole lysate is in a composition that is in the form of an aqueous solution, an aqueous-alcoholic solution, an oily solution, a solution dispersion, a lotion dispersion, a serum dispersion, an O/W emulsion, an W/O emulsion, a cream, an aqueous gel, an anhydrous gel, a microemulsion, a microcapsule, a microparticle, or a vesicular dispersion.

* * * * *